(12) United States Patent
Lee et al.

(10) Patent No.: US 11,039,766 B2
(45) Date of Patent: Jun. 22, 2021

(54) APPARATUS AND METHOD FOR ESTIMATING BIOLOGICAL COMPONENT

(71) Applicant: SAMSUNG ELECTRONICS CO., LTD., Suwon-si (KR)

(72) Inventors: So Young Lee, Daejeon (KR); Sang Kyu Kim, Yongin-si (KR); Sang Kon Bae, Seongnam-si (KR); Yun S Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 807 days.

(21) Appl. No.: 15/810,916

(22) Filed: Nov. 13, 2017

(65) Prior Publication Data

US 2018/0146899 A1    May 31, 2018

(30) Foreign Application Priority Data

Nov. 30, 2016 (KR) .................. 10-2016-0161724

(51) Int. Cl.
*A61B 5/145* (2006.01)
*A61B 5/1459* (2006.01)
(Continued)

(52) U.S. Cl.
CPC ........ *A61B 5/14532* (2013.01); *A61B 5/1459* (2013.01); *A61B 5/1495* (2013.01); *A61M 5/1723* (2013.01); *G01N 33/66* (2013.01)

(58) Field of Classification Search
CPC ..... A61B 5/145; A61B 5/1459; A61B 5/1495; A61B 5/0075; A61B 5/1455;
(Continued)

(56) References Cited

U.S. PATENT DOCUMENTS

| 5,028,787 A | 7/1991 | Rosenthal et al. |
| 5,068,536 A | 11/1991 | Rosenthal |

(Continued)

FOREIGN PATENT DOCUMENTS

| JP | 2000-60803 A | 2/2000 |
| JP | 2003-302406 A | 10/2003 |

(Continued)

OTHER PUBLICATIONS

Communication dated Apr. 24, 2018 by the European Patent Office in counterpart European Patent Application No. 17202578.5.

*Primary Examiner* — Eric F Winakur
*Assistant Examiner* — Abid A Mustansir
(74) *Attorney, Agent, or Firm* — Sughrue Mion, PLLC

(57) ABSTRACT

An apparatus for non-invasively estimating a biological component is provided. The apparatus may include: a sensor configured to measure a calibration spectrum for a first duration and measure a biological component estimation spectrum for a second duration, based on light returning from an object; and a processor configured to remove a signal of a biological component from the calibration spectrum to obtain a background spectrum for the first duration, and estimate the biological component, based on the background spectrum and the biological component estimation spectrum, for the second duration in response to a command for measuring the biological component.

31 Claims, 16 Drawing Sheets

(51) Int. Cl.
*A61B 5/1495* (2006.01)
*A61M 5/172* (2006.01)
*G01N 33/66* (2006.01)

(58) Field of Classification Search
CPC ..... A61B 5/6803; A61B 5/681; A61B 5/6814; A61B 5/6825; A61B 5/6826; A61B 5/7203; A61B 5/7257; A61M 5/1723; G01N 33/66
See application file for complete search history.

(56) References Cited

U.S. PATENT DOCUMENTS

| | | | |
|---|---|---|---|
| 5,077,476 A | 12/1991 | Rosenthal | |
| 5,086,229 A | 2/1992 | Rosenthal et al. | |
| 5,204,532 A | 4/1993 | Rosenthal | |
| 5,218,207 A | 6/1993 | Rosenthal | |
| 5,237,178 A | 8/1993 | Rosenthal et al. | |
| 5,355,880 A * | 10/1994 | Thomas | A61B 5/02007 128/925 |
| 5,362,966 A | 11/1994 | Rosenthal et al. | |
| 5,365,066 A | 11/1994 | Krueger, Jr. et al. | |
| 5,436,455 A | 7/1995 | Rosenthal et al. | |
| 5,438,201 A | 8/1995 | Rosenthal et al. | |
| 5,574,283 A | 11/1996 | Quintana | |
| 5,576,544 A | 11/1996 | Rosenthal | |
| 6,066,847 A | 5/2000 | Rosenthal | |
| 6,157,041 A * | 12/2000 | Thomas | A61B 5/1455 250/573 |
| 6,574,425 B1 | 6/2003 | Weiss et al. | |
| 6,952,263 B2 | 10/2005 | Weiss et al. | |
| 7,041,468 B2 | 5/2006 | Drucker et al. | |
| 7,460,895 B2 | 12/2008 | Arnold et al. | |
| 8,140,139 B2 | 3/2012 | Grata et al. | |
| 9,037,206 B2 | 5/2015 | Grata et al. | |
| 2003/0023148 A1 | 1/2003 | Lorenz et al. | |
| 2003/0216627 A1 | 11/2003 | Lorenz et al. | |
| 2006/0206018 A1 | 9/2006 | Abul-Haj et al. | |
| 2006/0281982 A1 | 12/2006 | Grata et al. | |
| 2008/0072663 A1 * | 3/2008 | Keenan | A61B 5/150229 73/61.41 |
| 2010/0145173 A1 | 6/2010 | Alferness et al. | |
| 2010/0312176 A1 | 12/2010 | Lauer et al. | |
| 2016/0213290 A1 | 7/2016 | Park et al. | |
| 2017/0079565 A1 | 3/2017 | Choi et al. | |
| 2017/0303846 A1 * | 10/2017 | O'Brien | A61B 5/0075 |
| 2018/0064378 A1 | 3/2018 | Park et al. | |
| 2018/0106678 A1 | 4/2018 | Bae et al. | |

FOREIGN PATENT DOCUMENTS

| | | |
|---|---|---|
| JP | 2008-5988 A | 1/2008 |
| JP | 2010-540133 A | 12/2010 |
| KR | 1993-7001738 A | 6/1993 |
| KR | 10-2008-0026159 A | 3/2008 |
| KR | 10-2014-0094111 A | 7/2014 |
| KR | 10-1591072 B1 | 2/2016 |
| KR | 10-2016-0032789 A | 3/2016 |
| KR | 10-2016-0090579 A | 8/2016 |
| KR | 10-2017-0035675 A | 3/2017 |
| KR | 10-2018-0027006 A | 3/2018 |
| KR | 10-2018-0042700 A | 4/2018 |
| WO | 99/23479 A1 | 5/1999 |

* cited by examiner

APPARATUS AND METHOD FOR ESTIMATING BIOLOGICAL COMPONENT

CROSS-REFERENCE TO RELATED APPLICATION(S)

This application claims priority from Korean Patent Application No. 10-2016-0161724, filed on Nov. 30, 2016 in the Korean Intellectual Property Office, the disclosure of which is incorporated herein by reference in its entirety.

BACKGROUND

1. Field

Apparatuses and methods consistent with exemplary embodiments relate to estimating a biological component in a non-invasive manner.

2. Description of Related Art

Diabetes is a chronic disease that causes various complications and can be hardly cured, and hence people with diabetes are advised to check their blood glucose regularly to prevent complications. In particular, when insulin is administered to control blood glucose, the blood glucose levels may have to be closely monitored to avoid hypoglycemia and control insulin dosage. There are several ways to monitor glucose levels, from invasive finger pricking testing to non-invasive glucose monitoring without causing pain. The invasive method may provide high reliability in measurement, but may cause pain and inconvenience as well as an increased risk of disease infections due to the use of injection. Recently, extensive research has been conducted on non-invasive measurements of biological components, such as blood glucose, based on spectrum analysis without collecting blood.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided an apparatus for estimating a biological component including: a sensor configured to measure a calibration spectrum for a first duration and measure a biological component estimation spectrum for a second duration, based on light returning from an object; and a processor configured to remove a signal of a biological component from the calibration spectrum to obtain a background spectrum for the first duration, and estimate the biological component, based on the background spectrum and the biological component estimation spectrum, for the second duration in response to a command for measuring the biological component.

The sensor may include: a light source configured to emit the light to the object; and a detector configured to detect the light returning from the object and measure the calibration spectrum and the biological component estimation spectrum based on the detected light.

The sensor may be further configured to measure the calibration spectrum and the biological component estimation spectrum based on at least one of infrared spectroscopy and Raman spectroscopy.

The processor may include a calibrator configured to obtain the background spectrum by removing the signal of the biological component from the calibration spectrum.

The calibrator may be further configured to remove the signal of the biological component from the calibration spectrum based on Lambert-Beer's law.

The calibrator may be further configured to generate the signal of the biological component to obtain the background spectrum based on a biological component measurement value of the object received from an external device.

The biological component measurement value may be measured invasively by the external device.

Two or more of the biological measurement values may be received from the external device.

The calibrator may be further configured to extract a background signal from the obtained background spectrum and calibrate a prediction model based on the extracted background signal.

The calibrator may be further configured to extract the background signal based on at least one of principal component analysis, independent component analysis, non-negative matrix factorization, and auto-encoding.

The processor may further include a component estimator configured to apply the prediction model to the measured biological component estimation spectrum and estimate the biological component based on the prediction model.

The biological component may include at least one of blood glucose, cholesterol, neural fat, proteins, and uric acid.

The processor may include a quality manager configured to evaluate a quality of the measured biological component estimation spectrum and determine whether to estimate the biological component or recalibrate a prediction model according to the evaluated quality.

The quality manager may be further configured to evaluate the quality of the biological component estimation spectrum based on at least one of noise analysis and variation pattern analysis on the measured biological component estimation spectrum.

According to an aspect of another exemplary embodiment, there is provided a method of estimating a biological component, including: obtaining a calibration spectrum based on a first light returning from an object; removing a signal of a biological component from the calibration spectrum to obtain a background spectrum; measuring a biological component estimation spectrum to estimate the biological component based on a second light returning from the object in response to a command for measuring the biological component; and estimating the biological component based on the background spectrum and the biological component estimation spectrum.

The method may further include: receiving a biological component measurement value of the object from an external device; and generating the signal of the biological component for obtaining the background spectrum based on the received biological component measurement value.

The biological component measurement value may be measured invasively by the external device.

Two or more of the biological measurement values may be received from the external device.

The method may further include: extracting a background signal from the obtained background spectrum; and calibrating a prediction model based on the extracted background signal.

The estimating the biological component may include applying the measured biological component estimation spectrum to the prediction model to estimate the biological component.

The method may further include evaluating a quality of the measured biological component estimation spectrum and determining whether to estimate a biological component or recalibrate a prediction model according to the evaluated quality.

The processor may be further configured to collect the background spectrum as training data and calibrate a prediction model to estimate the level of the biological component based on the collected training data.

The processor may be further configured to collect a biological component measurement value of the object from the object as the training data.

The processor may be further configured to generate the signal of the biological component to obtain the background spectrum based on the biological component measurement value among the training data and remove the generated biological component signal from the calibration spectrum.

The processor may be further configured to extract a background signal from the background spectrum among the training data and calibrate the prediction model based on the extracted background signal.

The processor may be further configured to calibrate the prediction model using Lambert-Beer's law based on the background signal and a unit spectrum.

According to an aspect of another exemplary embodiment, there is provided a wearable device including: a main body; a spectrometer mounted in the main body and configured to measure a spectrum from an object; and a processor mounted in the main body and configured to calibrate a prediction model based on a background spectrum obtained by removing a signal of a biological component from the spectrum measured by the spectrometer and estimate the biological component based on the calibrated prediction model.

The wearable device may further include a display mounted in the main body and configured to display the estimated biological component.

The wearable device may further include an operator mounted in the main body and configured to receive a calibration command or a biological component estimation command from a user and transmit the received command to the processor.

The wearable device may further include a communicator mounted in the main body and configured to build a communication connection with an external device and receive a biological component measurement value of the object from the external device.

The biological component measurement value may be measured invasively by the external device.

Two or more of the biological measurement values may be received from the external device.

According to an aspect of another exemplary embodiment, there is provided a non-transitory computer readable storage medium storing a program that is executable by a computer to perform: obtaining a calibration spectrum based on a first light returning from an object; removing a signal of a biological component from the calibration spectrum to obtain a background spectrum; measuring a biological component estimation spectrum to estimate the biological component from a second light returning from the object in response to a command for measuring the biological component; and estimating the biological component based on the background spectrum and the biological component estimation spectrum.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
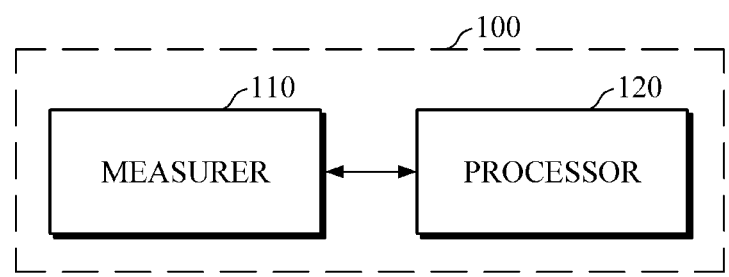
FIG. 1 is a block diagram illustrating an apparatus for estimating biological components according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are omitted to avoid obscuring the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the words "comprise" and "include" and their variations such as "comprises," "comprising", "includes," or "including," will be understood to imply the inclusion of stated elements but not the exclusion of any other elements. Terms such as " . . . unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list.

FIG. 1 is a block diagram illustrating an apparatus for estimating biological components according to an exemplary embodiment. The apparatus 100 for estimating biological components may be mounted in a wearable device which a user can wear. In this case, the wearable device may be of various types, such as a wrist watch type, a bracelet type, a wristband type, a ring type, an eyeglass type, a hair band type, or the like, and is not particularly limited in its shape, size, and the like.

Referring to FIG. 1, the apparatus 100 includes a measurer or sensor 110 and a processor 120.

The measurer 110 measures a spectrum of light reflected or scattered from an object. The measurer 110 may be implemented with an optical sensor. The object may be an upper part of a wrist where venous blood vessels or capillaries are located, or a region of the wrist surface adjacent to the radial artery. In the case of a skin area where the radial artery passes, the influences of external factors, such as the thickness of inner skin tissue on the wrist, which may cause a measurement error, may be relatively small. However, the object may not be limited to the above examples, and may be a peripheral part of the human body, such as a finger, a toe, or an earlobe, where the blood vessels are densely located.

In response to a specific control signal, the measurer 110 measures a spectrum by emitting light to the object and detecting light reflected or scattered from the object. In this case, the measurer 110 may use infrared spectroscopy or Raman spectroscopy, but is not limited thereto, and may measure the spectrum using various spectroscopy techniques.

Figure 2:
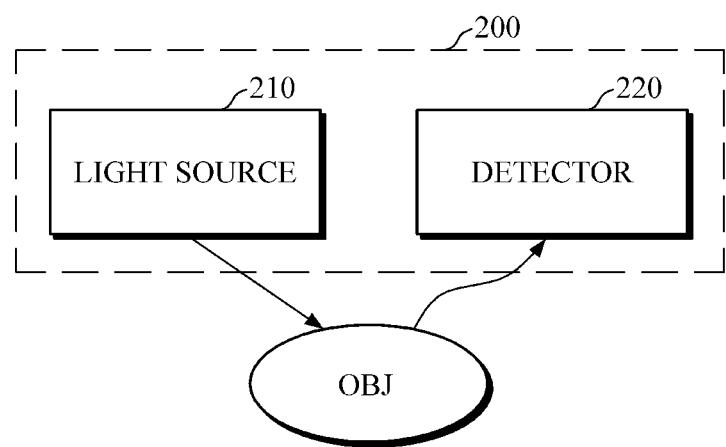
FIG. 2 is a block diagram of a measurer according to an exemplary embodiment.

FIG. 2 is a block diagram of a measurer according to an exemplary embodiment. FIG. 2 illustrates one exemplary embodiment of the measurer 110 of FIG. 1. The measurer 200 may be implemented with a spectrometer, a laser-based fluorescence sensor, or a glucose-sensing contact lens. Referring to FIG. 2, the measurer 200 includes a light source 210 and a detector 220.

The light source 210 may include a light emitting diode (LED), a laser diode, or a fluorescent body, and may emit light of a near-infrared ray (NIR) band or a mid-infrared ray (MIR) band. In particular, the light source 210 may include an array of a plurality of light sources which emit light of various wavelength bands in order to acquire accurate spectrum data. When the light source 210 emits light to the skin of a user, which is an object OBJ, in response to a control signal of the processor 120, the emitted light reaches a biological tissue, passing through the skin of the user. The light arriving at the biological tissue is scattered or reflected from the tissue and returns passing through the skin.

The detector 220 may detect the light returning from the skin of the user and measure a spectrum of the detected light. In this case, the detector 220 may be implemented with one or more InGaAs photodiodes, and a plurality of detectors may be provided.

The numbers and arrangements of the light sources 210 and the detectors 220 may vary, and may be altered according to a type of biological component, purpose of using the biological component, and the size and shape of a wearable device.

Referring back to FIG. 1, the processor 120 processes various signals and operations related to the estimation of biological component of the object OBJ. Here, the biological component may include blood glucose, neural fat, cholesterol, proteins, and uric acid, but is not limited thereto.

For example, the processor 120 may control the measurer 110 to measure a spectrum (hereinafter, will be referred to as a "biological component estimation spectrum") of light reflected or scattered from the object OBJ for biological component estimation in response to a biological component estimation command from the user. When the biological component estimation spectrum is measured, the processor 120 may calculate the biological component using the biological component estimation spectrum and a background spectrum. To acquire the background spectrum, a biological component signal may be removed from a calibration spectrum measured from the object OBJ.

In another example, upon a user's request for calibration, the processor 120 may control the measurer 110 to measure a calibration spectrum at predetermined intervals (e.g., 15 minutes) for a predetermined period of time (e.g., 4 hours). When the calibration spectrum is measured, the processor 120 may perform a calibration operation, such as acquiring the background spectrum by removing a biological component signal from the calibration spectrum.

Figure 3:
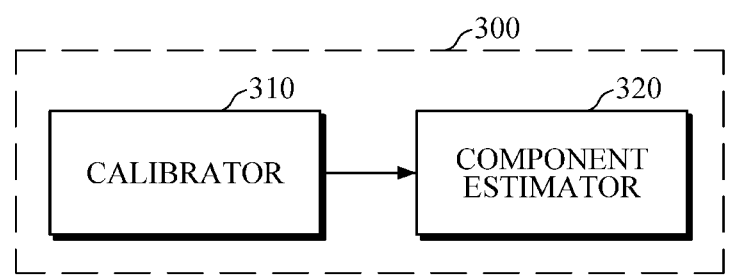
FIG. 3 is a block diagram illustrating a processor according to an exemplary embodiment.

FIG. 3 is a block diagram illustrating a processor according to one exemplary embodiment. A configuration of the processor 300 in accordance with one exemplary embodiment will be described in detail with reference to FIGS. 1 and 3.

Referring to FIG. 3, the processor 300 includes a calibrator 310 and a component estimator 320.

The calibrator 310 may perform a calibration operation for biological component estimation. For example, the calibrator 310 may control the measurer 110 to acquire a calibration spectrum when a user requests calibration or a preset standard is satisfied. The preset standard may be a calibration spectrum measurement interval (e.g., days, weeks, months, or the like), and the measurement may be set to be performed at a specific time period during a pertinent interval. The specific time period may be a fasting period, but is not limited thereto according to the exemplary embodiment. The specific time period may be preset so that the measurement can be performed at an appropriate time in consideration of a life pattern of a user.

The calibrator 310 may receive a plurality of calibration spectra from the measurer 110 and acquire background spectra as training data. For example, the calibrator 310 may remove a biological component signal from each of the acquired calibration spectra and acquire the resulting spectra as the background spectra.

In addition, the calibrator 310 may collect biological component measurement values measured by an external device as training data. The external device may be a device that invasively measures a biological component, but the type of the external device is not limited thereto. When a calibration operation is started upon the calibration request or according to the preset standard, the user may control the external device to measure a biological component. For example, using the external device, the user may measure the biological component each time the measurer 110 measures a calibration spectrum.

For instance, the calibrator 310 may control a communication module to build a communication connection with the external device, and may receive a measured biological component value when the external device completes the measurement of the biological component. In this case, the communication module may be based on Bluetooth communication, Bluetooth low energy (BLE) communication, near-field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, 5G communication, but is not limited thereto.

In another example, the calibrator 310 may receive the biological component measurement value measured by the external device from the user through an interface module. For example, the interface module may include a display which allows text input or a microphone which allows voice input.

Meanwhile, when the calibrator 310 receives a biological component measurement value that corresponds to each calibration spectrum, the calibrator 310 may generate a biological component signal on the basis of the received biological component measurement value. For example, the calibrator 310 may generate a biological component signal using the biological component measurement value, a unit biological component spectrum, and a light transmission path. In addition, when the biological component signal is generated, the calibrator 310 may acquire the background spectrum by removing the generated biological component signal from the calibration spectrum. In particular, the calibrator 310 may remove the biological component signal from the calibration spectrum using the Lambert-Beer's law.

When the background spectrum is acquired, the calibrator 310 may extract a background signal from the acquired background spectrum. In this case, the calibrator 310 may extract the background signal from the background spectrum using principal component analysis (PCA), independent component analysis (ICA), non-negative matrix factorization, auto-encoding, and the like.

When the background signal is extracted, the calibrator 310 may generate a prediction model for biological component estimation or calibrate a previously generated prediction model using the extracted background signal, the unit biological component spectrum, and the light transmission path. The prediction model may be in the form of a mathematical function expression based on the Lambert-Beer's law, but is not limited thereto.

The component estimator 320 may estimate a biological component using the prediction model generated or calibrated by the calibrator 310. When the measurer 110 measures a biological component estimation spectrum upon a user's request for biological component estimation, the component estimator 320 may receive the biological component estimation spectrum from the measurer 110 and obtain a biological component of interest by applying the prediction model to the received biological component estimation spectrum.

Figure 4:
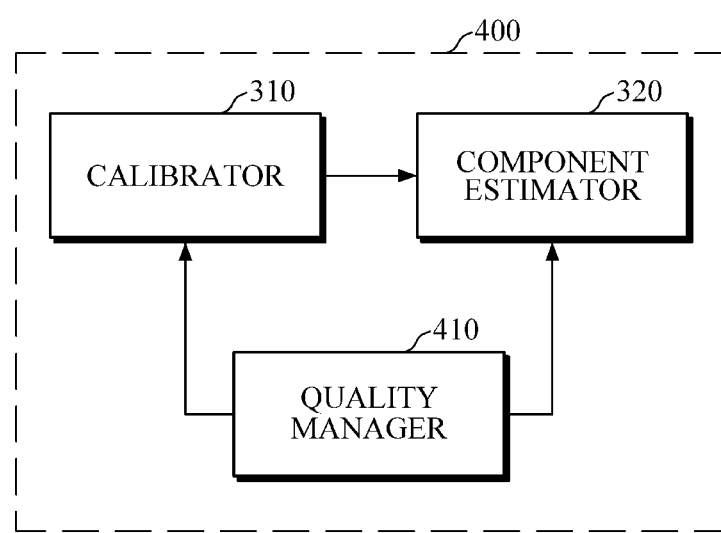
FIG. 4 is a block diagram illustrating a processor according to another exemplary embodiment.

FIG. 4 is a block diagram illustrating a processor according to another exemplary embodiment.

A configuration of a processor in accordance with another exemplary embodiment will be described with reference to FIGS. 1 and 4. The processor 400 may further include a quality manager 410 in addition to the calibrator 310 and the component estimator 320 of FIG. 3. The calibrator 310 and the component estimator 320 are described with reference to FIG. 3, and hence detailed description thereof will be omitted.

When the measurer 110 measures the biological component estimation spectrum upon a request for biological component estimation, the quality manager 410 may evaluate a quality of the measured biological component estimation spectrum before transmitting it to the component estimator 320. According to the evaluation result, the quality manager 410 may allow the component estimator 320 to estimate a biological component or allow the measurer 110 to re-measure a biological component estimation spectrum. Alternatively, the quality manager 410 may allow the calibrator 310 to re-perform the calibration operation on the prediction model.

When the calibrator 310 controls the measurer 110 to acquire a plurality of calibration spectra in order to calibrate the prediction model, the quality manager 410 may analyze the plurality of acquired calibration spectra to determine whether to continue to perform the calibration operation or re-perform the calibration operation at a different time period.

For example, in order to determine whether to recalibrate the prediction model, the quality manager 410 may evaluate qualities of a plurality of evaluation spectra. To obtain the evaluation spectra, the quality manager 410 may control the measurer 110 to measure the plurality of evaluation spectra at predetermined intervals for a predetermined time period either upon a user's request or at a preset interval. When the evaluation result shows that the qualities of the evaluation spectra do not satisfy a preset standard, the quality manager 410 may control the calibrator 310 to recalibrate the prediction model.

When the biological component estimation spectrum or the plurality of evaluation spectra are transmitted from the measurer 110, the quality manager 410 may evaluate the quality of the acquired spectrum using noise analysis or variation pattern analysis on the transmitted spectrum. For example, the quality manager 410 may calculate a noise of the acquired spectrum, and may perform recalibration when the noise exceeds a specific baseline. In another example, the quality manager 410 may convert the acquired time domain spectrum into a frequency domain spectrum by performing fast Fourier transform (TTF), and may determine to perform recalibration when a low-frequency random noise is detected in the resultant frequency domain spectrum.

In yet another example, the quality manager 410 may calculate mutual similarities between a plurality of spectra, and determine whether to perform recalibration on the basis of the calculated similarities. The quality manager 410 may determine to perform recalibration when a statistical value (e.g., an average, a maximum value, a minimum value, a variance, a standard deviation, etc.) of the calculated mutual similarities between the spectra is lower than a specific baseline. Alternatively, on the basis of the amount of change in the calculated similarities, the quality manager 410 may determine whether each spectrum has changed rapidly according to the elapse of measurement time, and may determine to perform recalibration when the spectrum is determined to be changed abruptly. Specifically, the quality manager 410 may compare a measured rate of the spectrum change to a predetermined rate, and may determine to perform recalibration when the measured rate of the spectrum change is greater than the predetermined rate. Further, the similarities may be calculated using a similarity calculation algorithm including Euclidean distance, Manhattan distance, cosine distance, Mahalanobis distance, Jaccard coefficient, extended Jaccard coefficient, Pearson's correlation coefficient, and Spearman's correlation coefficient.

Hereinafter, estimation of blood glucose, as an example of biological components, will be described with reference to FIGS. 5A to 6D.

Figure 5A:
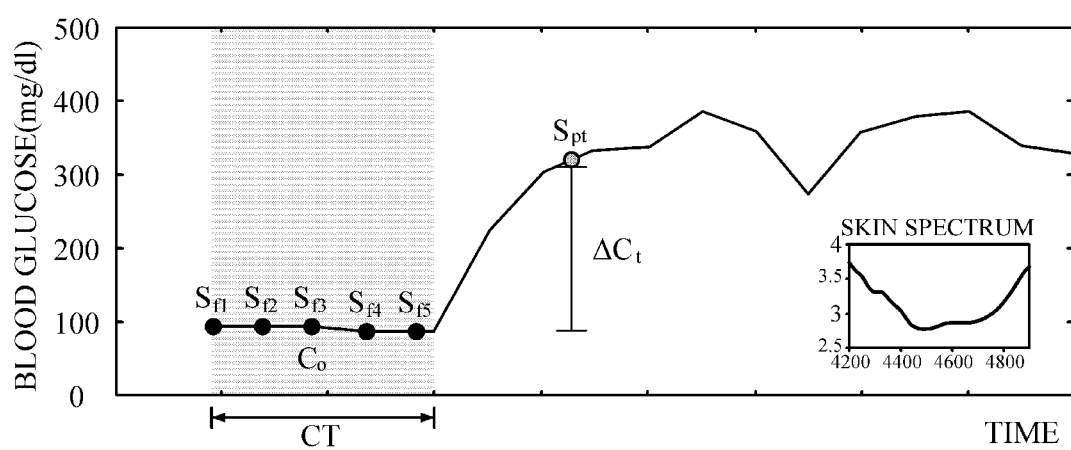
FIG. 5A is a diagram for describing a calibration method suitable for a fasting period.
Figure 5B:
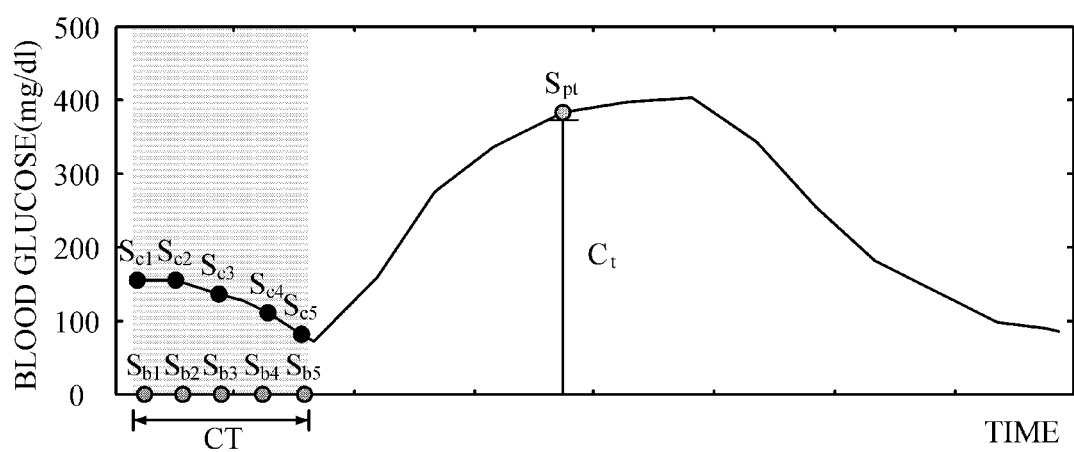
FIG. 5B is a diagram for describing a calibration method suitable both for fasting period and non-fasting period.

FIG. 5A is a diagram for describing a calibration method suitable for a fasting period. FIG. 5B is a diagram for describing a calibration method suitable both for a fasting period and non-fasting period.

FIG. 5A shows that a blood glucose estimation apparatus obtains five calibration spectra $S_f = \{S_{f1}, S_{f2}, S_{f3}, S_{f4}, S_{f5}\}$ for calibration at predetermined time intervals for a reference time period CT. The reference time period CT corresponds to a fasting period, and it is assumed that a blood glucose level $C_0$ during the fasting period is maintained substantially constant. Because $C_0$ is assumed constant, an external device may need to make its invasive measurement only once during the fasting period.

The blood glucose estimation apparatus may acquire background signals $BS = \{BS_1, BS_2, BS_3, BS_4, BS_5\}$ from the obtained calibration spectra $S_f$. In this case, the background signals may be obtained using a principal component analysis technique. In addition, the number of obtained background signals is not limited to five, and may be an arbitrary number. Once the background signals BS are obtained, a prediction model is generated using the Lambert-Beer's law, as shown in Equation 1, and blood glucose may be estimated through Equation 2.

$$S_{pt} = b_1 BS_1 + b_2 BS_2 + b_3 BS_3 + b_4 BS_4 + b_5 BS_5 + \varepsilon_g L_t \Delta C_t \quad (1)$$

$$C_t = \Delta C_t + C_0 \quad (2)$$

Here, $S_{pt}$ denotes a skin spectrum measured at an actual measurement time point t. $\varepsilon_g$ denotes a spectrum of pure glucose of unit concentration, and $L_t$ denotes a light transmission path. Hereinafter, $\varepsilon_g$ will be referred to as unit blood glucose spectrum. The unit blood glucose spectrum $\varepsilon_g$ and the light transmission path $L_t$ are input to the apparatus 100 in advance. $\Delta C_t$ denotes a difference between blood glucose $C_t$ to be actually measured and the fasting blood glucose $C_0$. $b_1, b_2, b_3, b_4, b_5$ denote coefficients of background signals $BS_1, BS_2, BS_3, BS_4, BS_5$, respectively, which are calculated using a least square method or the like.

In other words, when a skin spectrum is measured at the actual blood glucose measurement time point t, the blood glucose estimation apparatus may apply the skin spectrum to Equation 1 to estimate a blood glucose signal $\varepsilon_g L_t \Delta C_t$, and may calculate the amount of change in blood glucose at the time point t by using the unit blood glucose spectrum and the light transmission path $L_t$. Because, it is assumed that the fasting blood glucose is maintained constant, so when the amount of change in blood glucose $\Delta C_t$ is calculated, it is possible to estimate the blood glucose $C_t$ at the time point t by applying the calculated amount of change in blood glucose $\Delta C_t$ to Equation 2.

While, it is assumed that a baseline blood glucose level for calibration is constant during a fasting period, it is difficult to obtain a period of time during which the blood glucose level is actually maintained constant. In addition, a fasting period occurs mostly at dawn so that it is inconvenient to measure a spectrum. Furthermore, if blood glucose levels fluctuate even with fasting, it is difficult to accurately calibrate the prediction model. For example, in the case of diabetic patients who require accurate blood glucose estimation, the fasting blood glucose level is often not maintained constant. Therefore, the diabetic patients may need a blood glucose estimation method that does not assume a constant blood glucose level during a fasting period.

Estimation of blood glucose regardless of fasting will be described with reference to FIGS. 1 and 5B.

FIG. 5B illustrates five calibration spectra $S_c = \{S_{c1}, S_{c2}, S_{c3}, S_{c4}, S_{c5}\}$ obtained in a reference state CT for calibration, but the number of calibration spectra is not limited thereto. The reference state CT for calibration may or may not be a fasting period. The blood glucose in the reference state CT is not assumed to be constant, as described below.

When the calibration spectra $S_c$ are obtained, the apparatus 100 may acquire background spectra $S_b = \{S_{b1}, S_{b2}, S_{b3}, S_{b4}, S_{b5}\}$ by eliminating a blood glucose signal $\varepsilon_g L_t C_m$ from the calibration spectra $S_c$, as shown in the following Equation 3.

$$S_b = S_c - \varepsilon_g L_t C_m \quad (3)$$

Here, $\varepsilon_g$ denotes a unit blood glucose spectrum, and $L_t$ denotes a light transmission path. The unit blood glucose spectrum and the light transmission path are values which are input in advance. $C_m$ denotes a real blood glucose value measured invasively by an external device. In other words, an external device may need to make invasive measurements two times or more for calibration. The real blood glucose value may be measured at the time of measuring a calibration.

Then, the apparatus 100 may acquire background signals $BS = \{BS_1, BS_2, BS_3, BS_4, BS_5\}$ from the background spectra $S_b$ obtained using a principal component analysis. When the background signals BS are obtained, the apparatus 100 may generate a prediction model using the Lambert-Beer's law, as shown in Equation 4. When a spectrum $S_{pt}$ is measured at time t at which a real blood glucose is to be measured, the apparatus 100 may estimate the blood glucose signal $\varepsilon_g L_t C_t$ by applying the prediction model to the spectrum $S_{pt}$. When the blood glucose signal $\varepsilon_g L_t C_t$ is obtained as described above, a desired blood glucose value $C_t$ may be estimated based on the unit blood glucose spectrum and the light transmission path. $b_1, b_2, b_3, b_4, b_5$ denote coefficients of the background signals $BS_1, BS_2, BS_3, BS_4, BS_5$, respectively, which are calculated using a least square method.

$$S_{pt} = b_1 BS_1 + b_2 BS_2 + b_3 BS_3 + b_4 BS_4 + b_5 BS_5 + \varepsilon_g L_t C_t \quad (4)$$

According to the embodiment, a constant baseline blood glucose level is not required, so that it is possible to perform calibration without time constraints.

FIGS. 6A to 6D are graphs for describing estimation of a biological component according to different calibration time points.

Figure 6A:
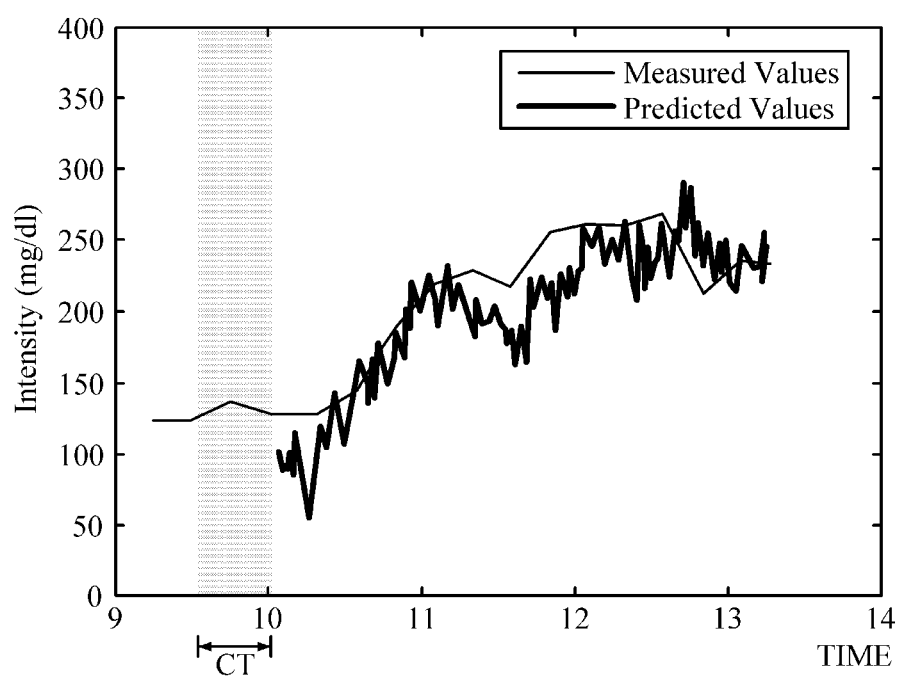
FIGS. 6A, 6B, 6C, and 6D are graphs for describing estimation of a biological component according to different calibration time points.
Figure 6B:
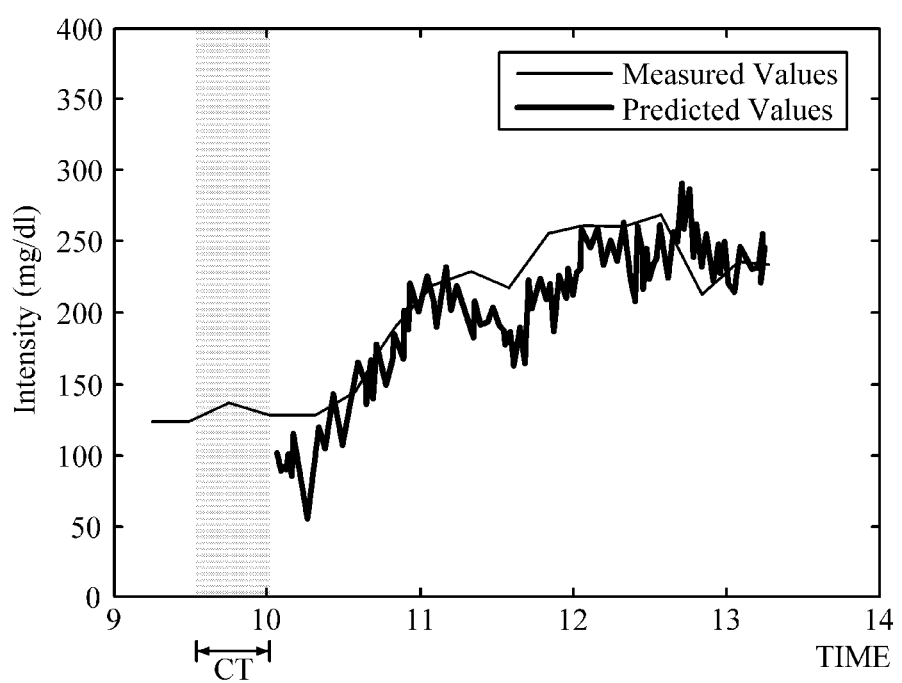

FIG. 6A shows result of estimation of a blood glucose level assuming a constant blood glucose level during the fasting time period CT. FIG. 6B show the result when no such assumption was made. In the case of FIG. 6A, a correlation R between the actual measurement value and a prediction value is 0.893, while in the case of FIG. 6B, the Pearson correlation coefficient R is 0.885. Therefore, it is seen that both methods result in accurate blood glucose measurement.

Figure 6C:
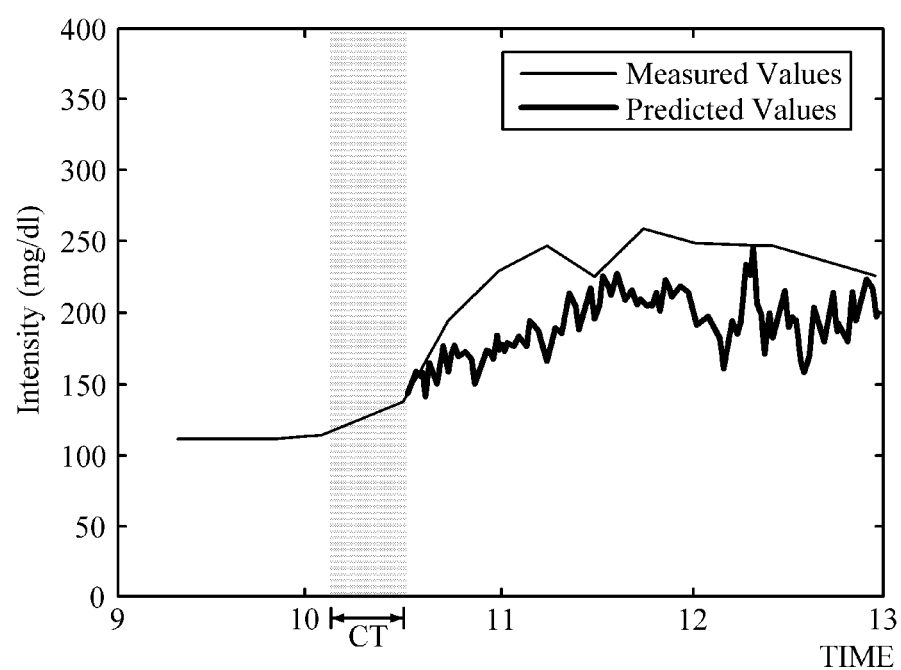
Figure 6D:
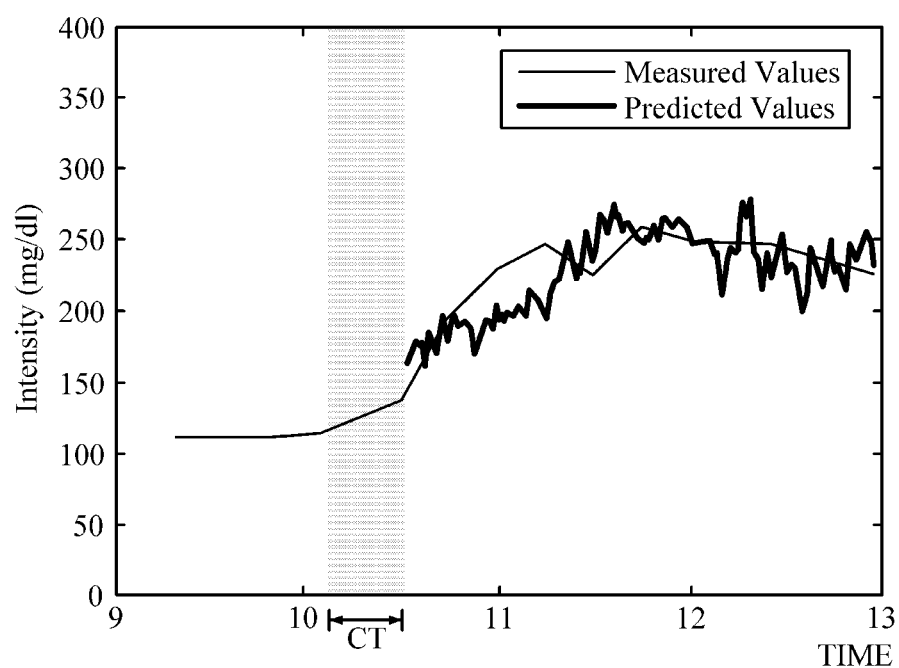

FIGS. 6C and 6D show results of estimation of a blood glucose level in a time period during which the blood glucose level is not maintained constant. In the case of FIG. 6C where a constant blood glucose level is assumed for the calibration period CT, a correlation R between the actual measurement value and a prediction value is 0.608, while in the case of FIG. 6D where no such assumption is made, the Pearson correlation coefficient R is 0.728. Thus, it is seen that the blood glucose measurement result making no constant blood glucose level is more accurate.

Figure 7:
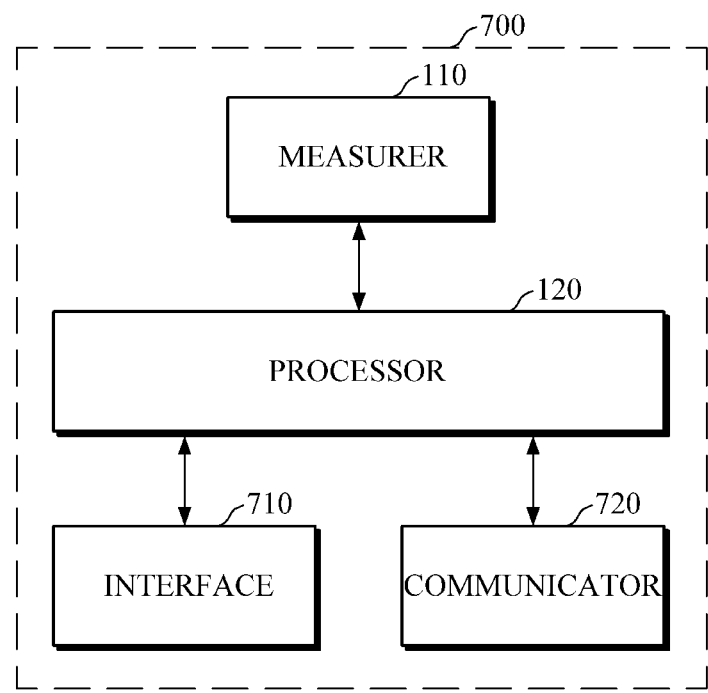
FIG. 7 is a block diagram illustrating an apparatus for estimating a biological component according to another exemplary embodiment.

FIG. 7 is a block diagram illustrating an apparatus for estimating a biological component according to another exemplary embodiment.

Referring to FIG. 7, an apparatus 700 for estimating a biological component includes a measurer 110, a processor 120, an interface 710, and a communicator 720. The configurations of the measurer 110 and the processor 120 are described in detail with reference to FIG. 1 and the following drawings, and hence the description will be made in focus with the interface 710 and the communicator 720.

The interface 710 interacts with a user using an interface module. For example, the interface module may include a display, a speaker, a microphone, a haptic device, and the like, but is not limited thereto.

The interface 710 may provide a user interface that allows a user to input a command related to biometric component estimation. For example, the interface 710 may provide a user interface that guides the user to input a command through a touch input to a display or through a separate operation module. In addition, in the case in which a wearable device includes voice recognition features, the interface 710 may output guide information through a speaker so that the user can input a command by voice.

The interface 710 may transmit the command input from the user to the processor 120 and provide a processing result from the processor 120 to the user through the user interface. In this case, the interface 710 may provide biological component information or warning or alarm information using a visual method, such as an output color, or a non-visual method, such as a vibration, a tactile sensation, voice, or the like. For example, a level of the blood glucose value and an output method for each level may be set in advance according to the user's characteristics, such as a user's health status. When the blood glucose value is estimated by the processor 120, the interface 710 may provide the pertinent information to the user using an output method corresponding to the level in which the estimated blood glucose value is present.

The communicator 720 may access a wireless communication network under the control of the processor 120 and may build a communication connection with an external device. In this case, the external device may include various information processing devices, such as a smartphone, a tablet PC, a desktop PC, and a notebook PC, in addition to a device that invasively measures a biological component, as described above.

The processor 120 may receive a biological component value measured by the external device. In addition, the processor 120 may transmit spectrum data measured by the measurer 111 or data related to the estimated biological component to the external device, and the external device may use the received data in monitoring of the user's health status. For instance, the external device may manage a history of changes in the biological component, e.g., a blood glucose level, and provide relevant information to the user in various ways, such as a graph.

Figure 8:
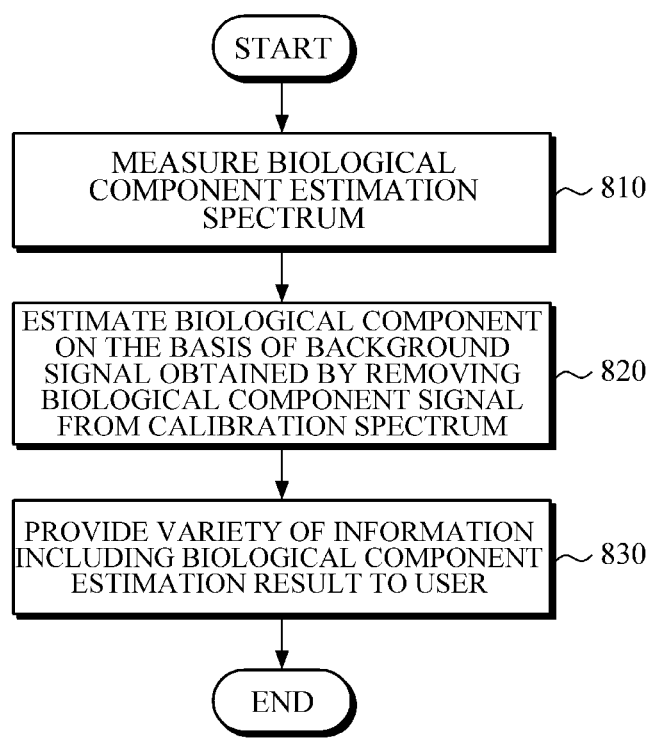
FIG. 8 is a flowchart illustrating a method of estimating a biological component according to an exemplary embodiment.

FIG. 8 is a flowchart illustrating a method of estimating a biological component according to one exemplary embodiment.

The method illustrated in FIG. 8 may be one exemplary embodiment performed by the apparatus 100 for estimating a biological component shown in FIG. 1. As described above in detail, the method will be described in brief to avoid redundancy.

Referring to FIG. 8, the apparatus 100 measures a biological component estimation spectrum from a user's skin upon a user's request, in operation 810.

In operation 820, the apparatus 100 removes a biological component signal from a calibration spectrum to obtain a background spectrum, and measures the biological component based on the background spectrum. For example, when the biological component estimation spectrum is measured, the apparatus 100 may estimate the biological component using a prediction model which has been calibrated through calibration process. The prediction model may be calibrated based on the background spectrum obtained from a calibration spectrum measured as described with reference to FIG. 9.

Thereafter, the apparatus 100 provides a variety of information including a biological component estimation result to the user, in operation 830.

Figure 9:
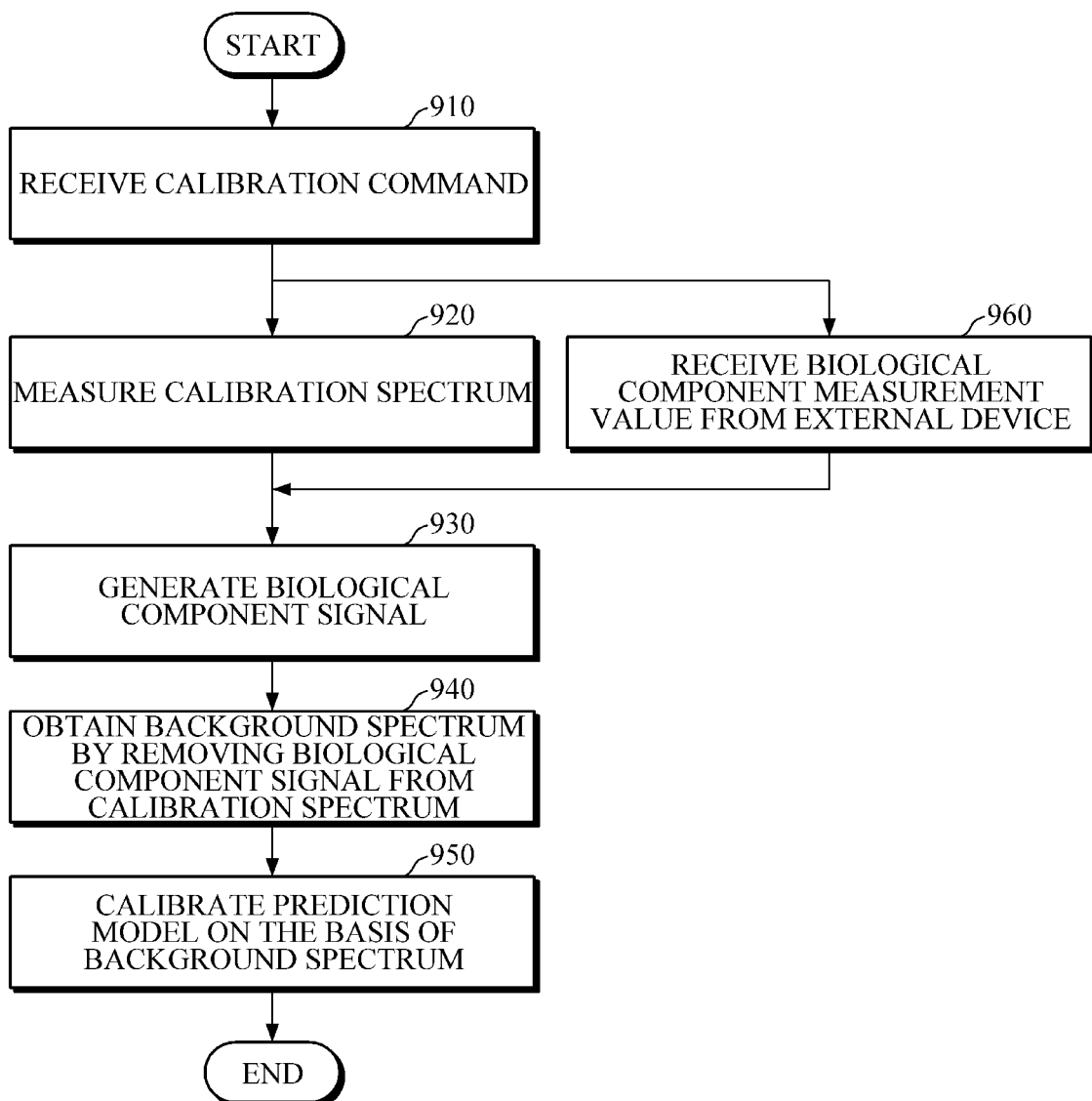
FIG. 9 is a flowchart illustrating a calibration method according to one exemplary embodiment.

FIG. 9 is a flowchart illustrating a calibration method according to one exemplary embodiment.

The method illustrated in FIG. 9 is one exemplary embodiment of a calibration method performed by the apparatus 100 of FIG. 1.

When the apparatus 100 for estimating a biological component receives a calibration command in operation 910, the apparatus 100 controls a light source and a detector to measure a calibration spectrum from an object, in operation 920. The calibration command may be input by a user, but is not limited thereto. A calibration interval may be set in advance according to necessity. A plurality of calibration spectra may be measured at predetermined intervals for a predetermined time period.

When the calibration command is received in operation 910, the apparatus 100 receives biological component measurement values from an external device and may collect the received biological component measurement values as training data, in operation 960. The external device may be a device that invasively measures a biological component, and the apparatus 100 may be connected to the external device using a mounted communication module. Alternatively, the apparatus 100 may provide an interface to the user to receive the biological component measurement value through an interface module and may receive the biological component measurement values measured by the external device from the user. The external device may measure the biological component value each time the apparatus 100 acquires a calibration spectrum.

Thereafter, the apparatus 100 generates a biological component signal using the biological component measurement value measured by the external device in operation 930. At this time, the biological component signal may be generated using the received biological component measurement value and the unit biological component spectrum and the light transmission path which have been input to the apparatus 100 in advance.

In operation 940, the apparatus 100 acquires a background spectrum by eliminating the biological component signal from the measured calibration spectrum and collects the acquired background spectrum as training data. For example, the apparatus 100 may remove the biological component signal from the calibration spectrum using the Lambert-Beer's law.

In operation 950, the apparatus 100 generates or calibrates a prediction model for biological component estimation on the basis of the acquired background spectrum. For example, the apparatus 100 may acquire a background signal from the background spectrum using principal component analysis and calibrate the prediction model into the form of a mathematical expression on the basis of the acquired background signal, using the Lambert-Beer's law.

Figure 10:
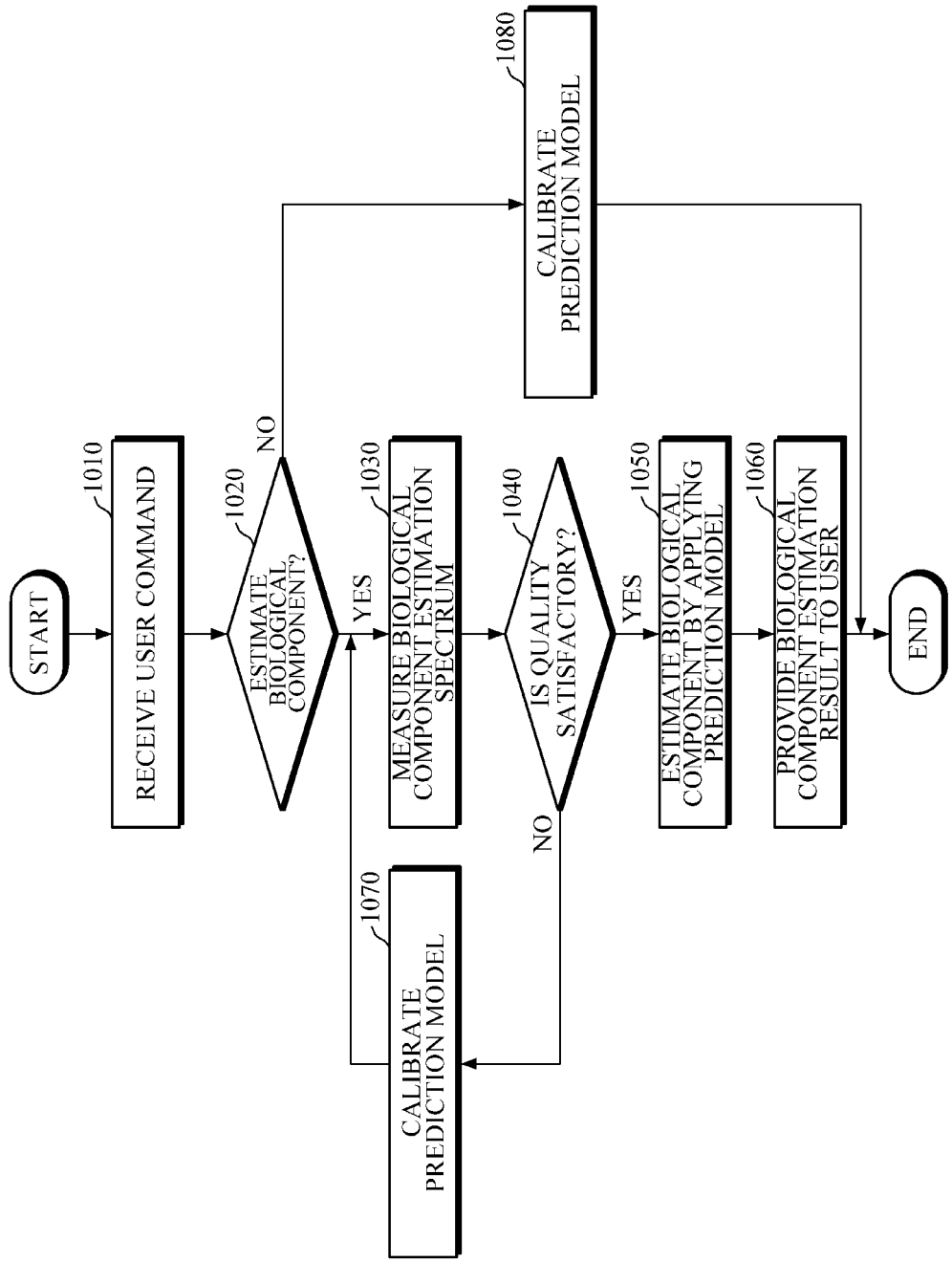
FIG. 10 is a flowchart illustrating a method of estimating a biological component according to another exemplary embodiment.

FIG. 10 is a flowchart illustrating a method of estimating a biological component according to another exemplary embodiment.

The method illustrated in FIG. 10 may be another embodiment of the method of estimating a biological component performed by the apparatus 100 of FIG. 1.

Referring to FIG. 10, the apparatus 100 for estimating a biological component receives a command from a user, as depicted in 1010, and determines whether the received command is a command for estimating a biological component or a calibration command, as depicted in 1020.

If the command is for estimating a biological component, the apparatus 100 emits light to the user's skin, by driving a light source and measures a biological component estimation spectrum on the basis of a light signal detected by a detector, in operation 1030.

Then, the apparatus 100 evaluates a quality of the measured biological component estimation spectrum and determines whether the biological component estimation spectrum is suitable for estimating a biological component, in operation 1040. For example, the apparatus 100 may calculate a noise of the biological component measurement spectrum and determine whether the quality of the biological component measurement spectrum is satisfactory or not according to whether or not the noise exceeds a predetermined standard. Alternatively, the apparatus 100 may calculate similarities between a plurality of biological component estimation spectra measured for a predetermined time period, identify the variation pattern of each spectrum over time on the basis of the similarities, and determine that a spectrum which has a change rate greater than a threshold change rate is not suitable for estimating a biological component. However, the exemplary embodiments are not limited to the above examples.

Then, when it is determined that the biological component estimation spectrum is suitable for estimating a biological component, the apparatus 100 measures a biological component by applying a prediction model to the biological component estimation spectrum, which has been calibrated in advance, in operation 1050.

The, the apparatus 100 provides a biological component estimation result to the user, in operation 1060. The biological component estimation result may be displayed visually using colors, different line thicknesses, or various graphs. Alternatively, the biological component estimation result may be provided using a non-visual method, such as a voice, a tactile sensation, or a vibration.

If it is determined in operation 1040 that the quality of the biological component estimation spectrum measured is not suitable for estimating a biological component, the apparatus 100 may recalibrate the prediction model, as described above in reference with FIG. 9. In addition, when it is determined in operation 1020 that the user's command is a calibration command, the apparatus 100 recalibrates the prediction model in operation 1080.

Figure 11:
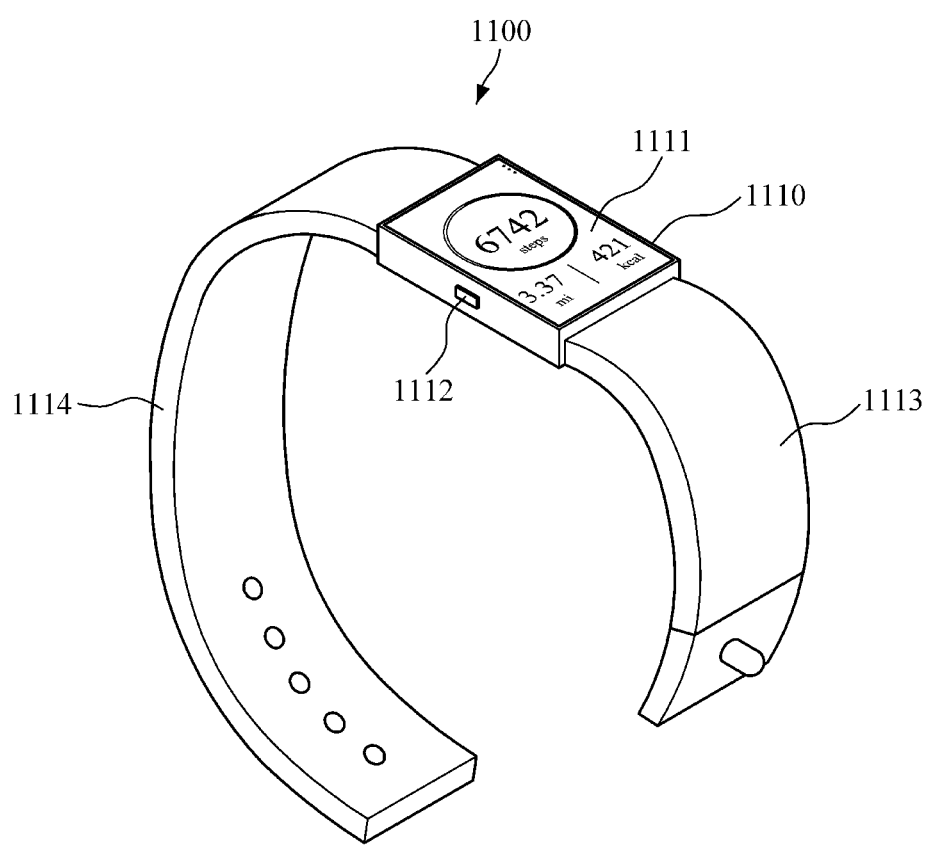
FIG. 11 is a diagram illustrating a wearable device according to an exemplary embodiment.
Figure 12:
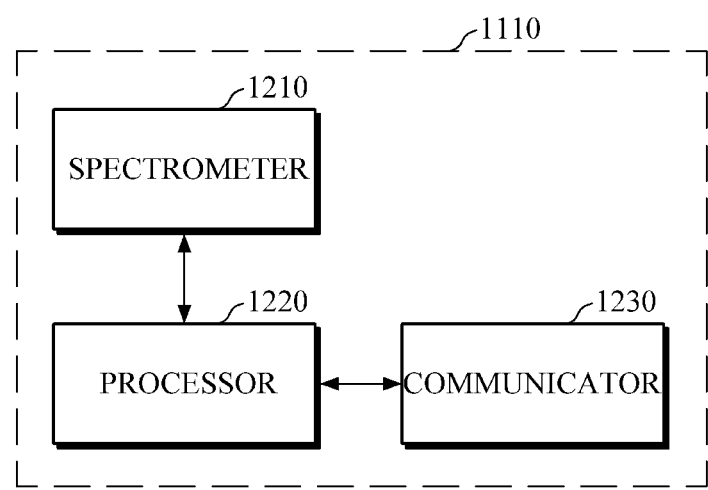
FIG. 12 is a block diagram illustrating a configuration mounted in a main body of the wearable device of FIG. 11.

FIG. 11 is a diagram illustrating a wearable device according to one exemplary embodiment. FIG. 12 is a block diagram illustrating a configuration mounted in a main body of the wearable device of FIG. 11.

As illustrated in FIGS. 11 and 12, various exemplary embodiments of the apparatus for estimating a biological component may be mounted in a smart band-type wearable device. However, it is purely one example for convenience of description, and it should not be construed that the exemplary embodiments are applied only to the smart band-type wearable device.

Referring to FIGS. 11 and 12, the wearable device 1100 includes a main body 1110 and a strap including strap members 1113 and 1114.

The strap may be formed to be flexible and be bent in such a manner that each strap member can be wrapped around and removed from a user's wrist. In this case, a battery for supplying power to the wearable device 100 may be embedded in the main body 1110 or the strap member 1114.

The main body 1110 of the wearable device 1100 may include a spectrometer 1210 and a processor 1220. The spectrometer emits light to the user's skin and measures a spectrum by dispersing the light scattered or reflected from the skin, and the processor 1220 estimates a user's biological component using the spectrum measured by the spectrometer 1210.

In response to a control signal, the processor 1220 drives the spectrometer 1210 to emit light to the skin of the user's wrist area and detects light returning from the skin. The light emitted from a light source reaches a biological tissue, passing through the user's skin, and the light arriving at the biological tissue reacts with the biological tissue and returns. The spectrometer 1210 obtains a spectrum of the returning light and transmits the spectrum to the processor 1220. In this case, the light source may be configured to emit light of an NIR band or an MIR band.

In addition, the spectrometer 1210 may include a linear variable filter (LVF). The LVF has a spectral characteristic that linearly changes over the entire length. Therefore, the LVF may disperse incident light in wavelength order. The LVF has a compact size and an excellent spectral performance.

The processor 1220 may process various commands once the commands are input through an operator 1112 or a display 1111. For example, when a calibration command is input by the user, calibration of a prediction model may be performed, as described above. In addition, when a biological component estimation command is input by the user, a biological component may be estimated based on the calibrated prediction model. In particular, the processor 1220 may evaluate the quality of an optical spectrum. When the quality of the measured spectrum is not suitable for estimating a biological component, calibration may be re-performed. In addition, the processor 1220 may generate a variety of healthcare information, such as warnings, alarms, and a history of changes in health status, on the basis of the estimated biological component information.

The operator 1112 mounted in the main body 1110 may receive a user's control command and transmit it to the processor 1220, and may include a power button for inputting a command for power on/off of the wearable device 1100.

The display 1111 mounted in the main body 1110 may provide a variety of information generated by the processor 1220, for example, information related to a biological component and other various types of information (e.g., time, weather, etc.) to the user under the control of the processor 1220.

The communicator 1230 may communicate with the external device under the control of the processor 1220. The external device may be an information processing device, such as a smartphone, a desktop computer, a notebook computer, or the like, which has superior computing performance. In addition, the external device may be an invasive biological component measurement device.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating a biological component, the apparatus comprising:
   a sensor configured to measure a calibration spectrum for a first duration and measure a biological component estimation spectrum for a second duration, based on light returning from an object; and
   a processor configured to:
      generate a signal of a biological component by using a unit spectrum of the biological component and at least one biological component measurement value;
      remove the signal of the biological component from the calibration spectrum to obtain a background spectrum for the first duration; and
      estimate the biological component, based on the background spectrum and the biological component estimation spectrum, for the second duration in response to a command for measuring the biological component.

2. The apparatus of claim 1, wherein the sensor comprises:
   a light source configured to emit the light to the object; and
   a detector configured to detect the light returning from the object and measure the calibration spectrum and the biological component estimation spectrum based on the detected light.

3. The apparatus of claim 2, wherein the sensor is further configured to measure the calibration spectrum and the biological component estimation spectrum based on at least one of infrared spectroscopy and Raman spectroscopy.

4. The apparatus of claim 1, wherein the processor comprises a calibrator configured to obtain the background spectrum by removing the signal of the biological component from the calibration spectrum.

5. The apparatus of claim 4, wherein the calibrator is further configured to remove the signal of the biological component from the calibration spectrum based on Lambert-Beer's law.

6. The apparatus of claim 4, wherein the calibrator is further configured to extract a background signal from the obtained background spectrum and calibrate a prediction model based on the extracted background signal.

7. The apparatus of claim 6, wherein the calibrator is further configured to extract the background signal based on at least one of principal component analysis, independent component analysis, non-negative matrix factorization, and auto-encoding.

8. The apparatus of claim 6, wherein the processor further comprises a component estimator configured to apply the prediction model to the measured biological component estimation spectrum and estimate the biological component based on the prediction model.

9. The method of claim 1, wherein the biological component measurement value is measured invasively.

10. The method of claim 9, wherein two or more biological component measurement values are received.

11. The apparatus of claim 1, wherein the biological component comprises at least one of blood glucose, cholesterol, neural fat, proteins, and uric acid.

12. The apparatus of claim 1, wherein the processor comprises a quality manager configured to evaluate a quality of the measured biological component estimation spectrum and determine whether to estimate the biological component or recalibrate a prediction model according to the evaluated quality.

13. The apparatus of claim 12, wherein the quality manager is further configured to evaluate the quality of the biological component estimation spectrum based on at least one of noise analysis and variation pattern analysis on the measured biological component estimation spectrum.

14. The apparatus of claim 1, wherein the processor is further configured to collect the background spectrum as training data and calibrate a prediction model to estimate a level of the biological component based on the training data.

15. The apparatus of claim 14, wherein the processor is further configured to collect the at least one biological component measurement value of the object as the training data.

16. The apparatus of claim 15, wherein the processor is further configured to generate the signal of the biological component to obtain the background spectrum based on the at least one biological component measurement value among the training data and remove the generated biological component signal from the calibration spectrum.

17. The apparatus of claim 14, wherein the processor is further configured to extract a background signal from the background spectrum among the training data and calibrate the prediction model based on the extracted background signal.

18. The apparatus of claim 17, wherein the processor is further configured to calibrate the prediction model using Lambert-Beer's law based on the background signal and a unit spectrum.

19. A method of estimating a biological component, comprising:
   obtaining a calibration spectrum based on a first light returning from an object;
   generate a signal of a biological component by using a unit spectrum of the biological component and at least one biological component measurement value;
   removing the signal of the biological component from the calibration spectrum to obtain a background spectrum;
   measuring a biological component estimation spectrum to estimate the biological component based on a second light returning from the object in response to a command for measuring the biological component; and estimating the biological component based on the background spectrum and the biological component estimation spectrum.

20. The method of claim 19, wherein the biological component measurement value is measured invasively.

21. The method of claim 20, wherein two or more biological component measurement values are received.

22. The method of claim 19, further comprising:
extracting a background signal from the obtained background spectrum; and
calibrating a prediction model based on the extracted background signal.

23. The method of claim 22, wherein the estimating the biological component comprises applying the measured biological component estimation spectrum to the prediction model to estimate the biological component.

24. The method of claim 19, further comprising evaluating a quality of the measured biological component estimation spectrum and determining whether to estimate a biological component or recalibrate a prediction model according to the evaluated quality.

25. A wearable device comprising:
a main body;
a spectrometer mounted in the main body and configured to measure a spectrum from an object; and
a processor mounted in the main body and configured to:
generate a signal of a biological component by using a unit spectrum of the biological component and at least one biological component measurement value;
calibrate a prediction model based on a background spectrum obtained by removing the signal of the biological component from the spectrum measured by the spectrometer; and
estimate the biological component based on the calibrated prediction model.

26. The wearable device of claim 25, further comprising a display mounted in the main body and configured to display the estimated biological component.

27. The wearable device of claim 25, further comprising an operator mounted in the main body and configured to receive a calibration command or a biological component estimation command from a user and transmit the received command to the processor.

28. The wearable device of claim 25, further comprising a communicator mounted in the main body and configured to build a communication to receive a biological component measurement value of the object.

29. The method of claim 28, wherein the biological component measurement value is measured invasively.

30. The method of claim 29, wherein two or more biological component measurement values are received.

31. A non-transitory computer readable storage medium storing a program that is executable by a computer to perform:
obtaining a calibration spectrum based on a first light returning from an object;
generate a signal of a biological component by using a unit spectrum of the biological component and at least one biological component measurement value;
removing the signal of the biological component from the calibration spectrum to obtain a background spectrum;
measuring a biological component estimation spectrum to estimate the biological component from based on a second light returning from the object in response to a command for measuring the biological component; and
estimating the biological component based on the background spectrum and the biological component estimation spectrum.

* * * * *